| United States Patent [19] | [11] Patent Number: 4,735,933 |
| Hudspeth et al. | [45] Date of Patent: Apr. 5, 1988 |

[54] RENIN INHIBITORS III

[75] Inventors: James P. Hudspeth; James S. Kaltenbronn; Joseph T. Repine; W. Howard Roark; Michael A. Stier, all of Ann Arbor, Mich.

[73] Assignee: Warner-Lambert Company, Morris Plains, N.J.

[21] Appl. No.: 941,966

[22] Filed: Dec. 15, 1986

[51] Int. Cl.⁴ .................. A61K 37/43; C07K 5/06; C07K 5/08
[52] U.S. Cl. .................................... 514/18; 530/330; 530/331
[58] Field of Search .................. 514/18; 530/330, 331

[56] References Cited

U.S. PATENT DOCUMENTS 4,479,941 10/1984 Veber et al. .................... 514/17

FOREIGN PATENT DOCUMENTS

85/115920 6/1986 European Pat. Off. .
85/308759 7/1986 European Pat. Off. .

Primary Examiner—Delbert K. Phillips
Attorney, Agent, or Firm—Elizabeth M. Anderson

[57] ABSTRACT

The invention concerns novel renin-inhibitory peptides which are useful for treating renin associated hypertension and hyperaldosteronism. Processes for preparing the peptides, compositions containing them and methods of using them are included. Also included is a diagnostic test using the compounds to determine the presence of renin-associated hypertension or hyperaldosteronism.

8 Claims, No Drawings

RENIN INHIBITORS III

BACKGROUND OF THE INVENTION

Renin is a natural enzyme which is released into the blood from the kidney. It cleaves its natural substrate, angiotensinogen, releasing a decapeptide, angiotensin I. This is in turn cleaved by converting enzyme in the lung, kidney and other tissues to an octapeptide, angiotensin II. Angiotensin II raises blood pressure both directly by causing arteriolar constriction and indirectly by stimulating release of the sodium-retaining hormone aldosterone from the adrenal gland causing a rise in extracellular fluid volume. Inhibitors of renins have been sought as an agent for control of hypertension and hyperaldosteronism.

The present invention concerns novel peptides which inhibit renin. It also concerns pharmaceutical compositions containing these novel peptides, methods of treating renin-associated hypertension and hyperaldosteronism, as well as the use of the peptides as diagnostic tools, and the methods for preparing the peptides.

U.S. Pat. No. 4,479,941 covers certain renin-inhibitory peptides of the formula

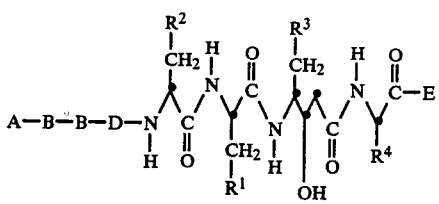

European Application No. 85/308759 covers certain renin-inhibitory dipeptides of the formula

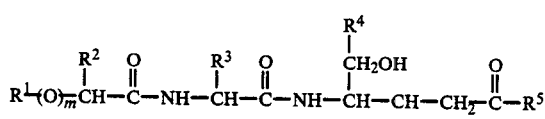

wherein m is 0 or 1 and $R^1$–$R^5$ are a variety of organic groups.

European Application No. 184,855 covers renin-inhibitory peptides of the formula

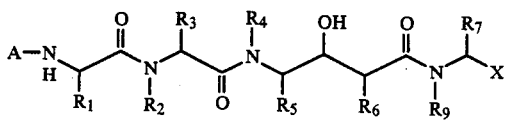

wherein A is an N-protecting group; $R_1$, $R_3$, $R_5$ and $R_7$ are loweralkyl or lipophilic or aromatic amino acid side chains and may be the same or different; $R_2$, $R_4$ and $R_6$ are hydrogen or loweralkyl and may be the same or different; X is hydrogen, loweralkyl or —CH$_2$OR$_8$, wherein $R_8$ is hydrogen, loweralkyl or alkaryl; and $R_9$ is loweralkyl, hydroxy, hydroxyalkyl, alkoxy, allyl, alkaryloxy or thioalkyl and pharmaceutically acceptable salts thereof.

SUMMARY OF THE INVENTION

The present invention relates to novel peptides of the formula

ACYL—X—Y—W—U     (I)

and the pharmaceutically acceptable acid addition salts thereof wherein ACYL, X, Y, W, and U are as defined herein below.

The invention also includes pharmaceutical compositions comprising an effective amount of the above peptide of formula I in admixture with a pharmaceutically acceptable carrier or excipient and a method for treating renin-associated hypertension in a patient suffering therefrom comprising administering to said patient the above pharmaceutical composition in unit dosage form.

Further the invention includes a pharmaceutical composition comprising an effective amount of a peptide of formula I above in admixture with a pharmaceutically acceptable carrier or excipient, and a method for treating hyperaldosteronism in a patient suffering therefrom comprising administering to said patient the above pharmaceutical composition in unit dosage form.

The present invention also includes the use of peptides of formula I above as diagnostic tools for the identification of cases of hypertension due to renin excess.

The invention further includes methods for preparing peptides of formula I above.

DETAILED DESCRIPTION

The following table provides a dictionary of the terms used in the description of the invention.

TABLE I

| Abbreviated Designation | Amino Acid |
| --- | --- |
| HIS | L—Histidine |
| D—HIS | D—Histidine |
| LEU | L—Leucine |
| D—LEU | D—Leucine |
| STA | 4(S)—Amino-3(S)—hydroxy-6-methylheptanoic acid |
| PHSTA | 4(S)—Amino-3(S)—hydroxy-5-phenylpentanoic acid |
| CYSTA | 4(S)—Amino-3(S)—hydroxy-5-cyclohexanepentanoic acid |
| ILE | L—Isoleucine |
| D—ILE | D—Isoleucine |
| N—MeHIS | N—Methylhistidine |
| N—MeLEU | N—Methylleucine |
| N—MeILE | N—Methylisoleucine |
| PHE | L—Phenylalanine |
| HOMOPHE | Homophenylalanine |
| HOMOHIS | Homohistidine |
| NLE | Norleucine |
| VAL | L—Valine |
| Protecting Group | |
| Z | Benzyloxycarbonyl |
| BOC | Tert-butyloxycarbonyl |
| TRT | Trityl |
| Acyl Group | |
| DNMA | Di-(1-naphthylmethyl)-acetyl |
| Amides With | |
| —NHCH$_2$Ph | Benzylamine |
| 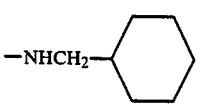 | Cyclohexylmethylamine |
| 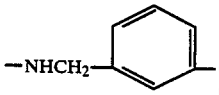 | m-Xylene-di-amine (Z or BOC) |

TABLE I-continued

| Abbreviated Designation | Amino Acid |
|---|---|
| 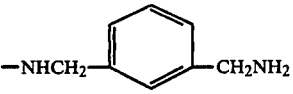 —NHCH₂-⌬-CH₂NH₂ | m-Xylene-di-amine |
| —NH₂ | Ammonia |
| —NH-⌬N—CH₂Ph | 4-Amino-N—benzyl-piperidine |
| —NH-⌬NH | 4-Aminopiperidine |
| —NH—CH₂-⌬N | 2-Aminomethylpyridine |
| —NHCH₂CHCH₂CH₃<br>   \|<br>   CH₃ | 2-Methylbutylamine |
| | Esters With |
| —OCH₃ | Methanol |
| —OC₂H₅ | Ethanol |

The peptides of the present invention are represented by the formula

ACYL—X—Y—W—U    I and the pharmaceutically acceptable acid addition salts thereof, wherein ACYL is DNMA,

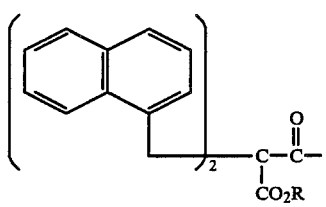

wherein R is hydrogen or a straight or branched lower alkyl of from one to six carbon atoms

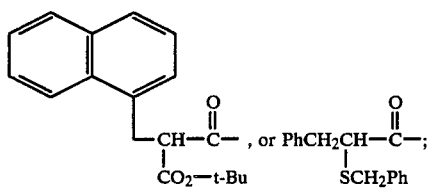

X is HIS, HOMOHIS, PHE, HOMOPHE, ILE, LEU, NLE, N-MeHIS, N-MeLEU, or

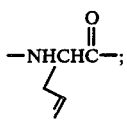
—NHCHC—;

Y is STA, CYSTA, or PHSTA;
W is LEU, ILE, N-MeLEU, N-MeILE, VAL or absent with the proviso that, when ACYL is DNMA, W is present; and
U is —NHCH₂CH(CH₃)CH₂CH₃, —NHCH₂Ph, —NHCH₂CH(OH)CH₂SCH(CH₃)₂, —NHCH₂CH(OH)CH₂SOCH(CH₃)₂, —NHCH₂CH(OH)CH₂SO₂CH(CH₃)₂,

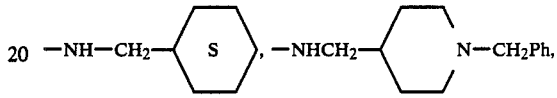

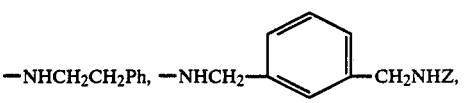

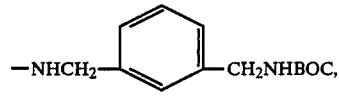

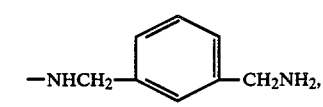

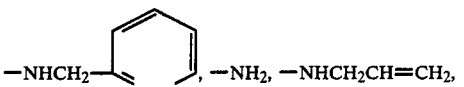

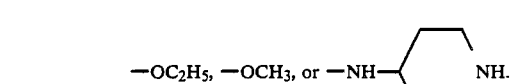

Preferred compounds of the present invention are compounds of formula I wherein U is
—NHCH₂Ph,

—NHCH₂CH=CH₂, —NHCH₂CH(OH)CH₂SCH(CH₃)₂,
—NHCH₂CH(OH)CH₂SOCH(CH₃)₂,
—NHCH₂CH(OH)CH₂SO₂CH(CH₃)₂, or
—NHCH₂CH(CH₃)CH₂CH₃.

Particularly valuable compounds falling within the scope of the invention include the following compounds, their isomers, and pharmaceutically acceptable acid addition salts: DNMA—HIS—STA—LEU—NHCH₂Ph,

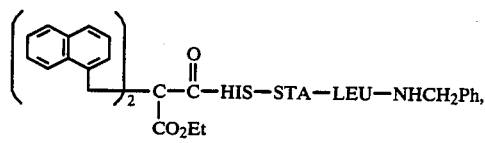
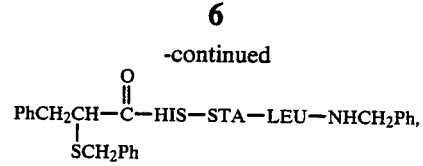
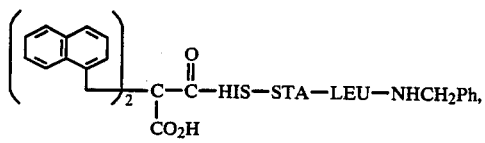
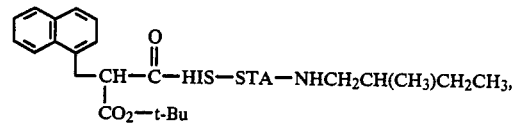
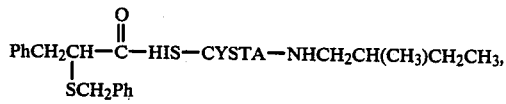
DNMA—HIS—STA—NHCH$_2$CH=CH$_2$,
DNMA—HIS—STA—NHCH$_2$CH(OH)CH$_2$SCH(CH$_3$)$_2$, or
DNMA—HIS—STA—NHCH$_2$CH(OH)CH$_2$SO$_2$CH(CH$_3$)$_2$.
Other compounds of the present invention include the following:
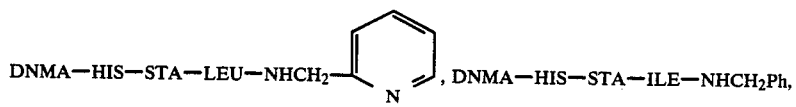
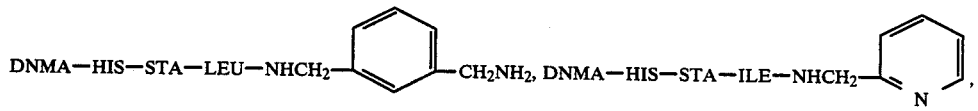
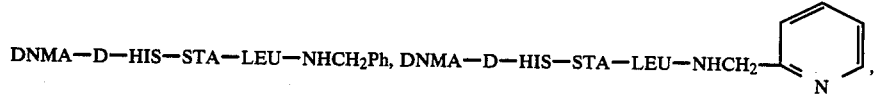
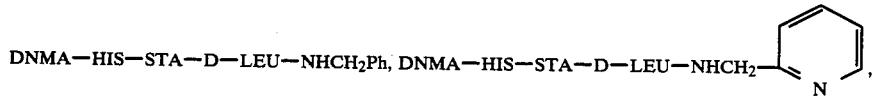
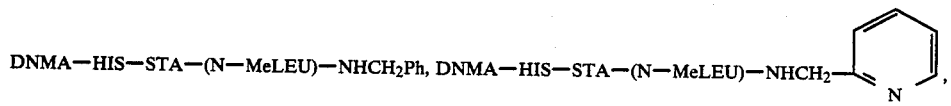
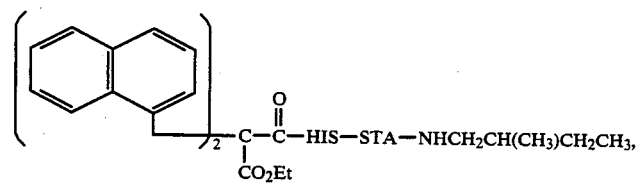
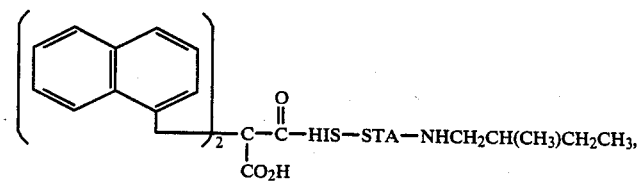
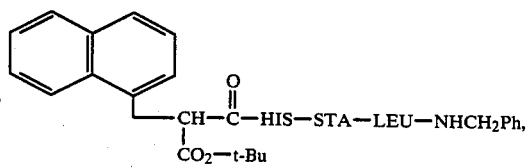

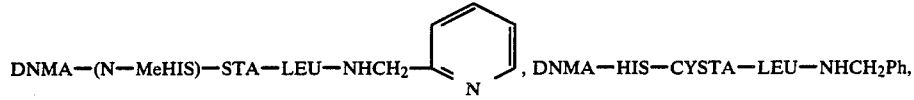, DNMA—HIS—CYSTA—LEU—NHCH₂Ph,

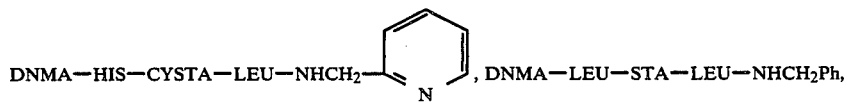, DNMA—LEU—STA—LEU—NHCH₂Ph,

DNMA—ILE—STA—LEU—NHCH₂Ph, DNMA—LEU—CYSTA—LEU—NHCH₂Ph,

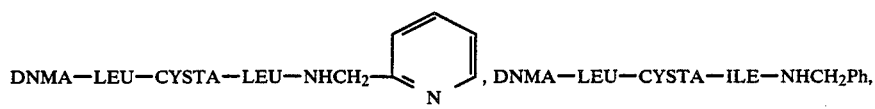, DNMA—LEU—CYSTA—ILE—NHCH₂Ph,

DNMA—HIS—CYSTA—ILE—NHCH₂Ph, DNMA—PHE—STA—LEU—NHCH₂Ph,
DNMA—HOMOHIS—CYSTA—LEU—NHCH₂Ph, DNMA—NLE—STA—LEU—NHCH₂Ph,

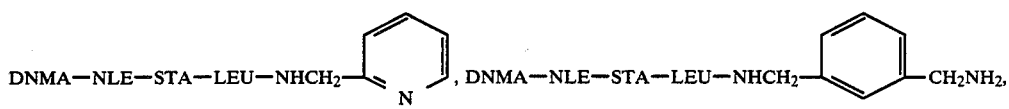

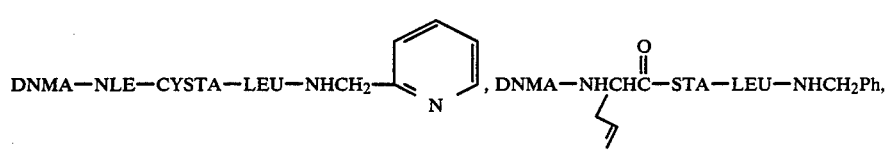

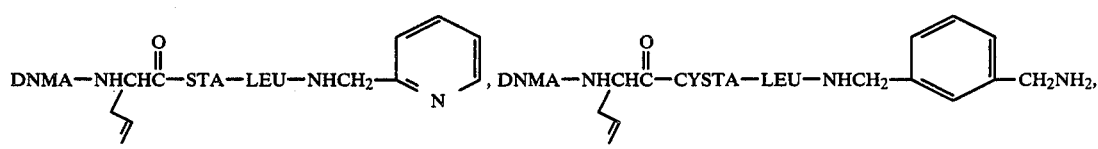

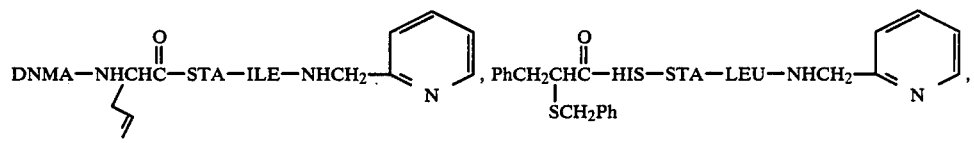

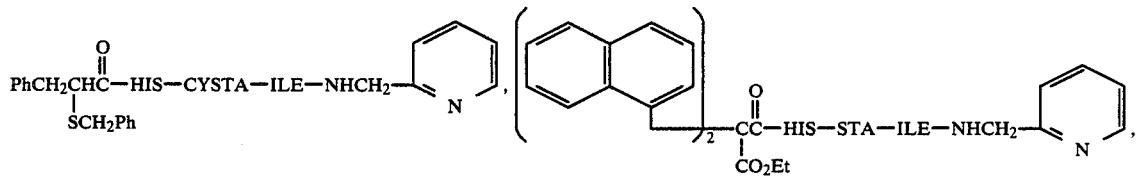

DNMA—(N—MeLEU)—STA—LEU—NHCH₂Ph,

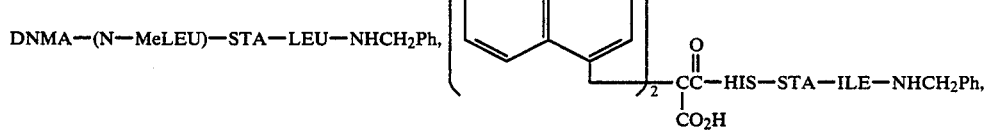

DNMA—HIS—PHSTA—LEU—NHCH₂Ph, DNMA—HIS—PHSTA—LEU—NHCH₂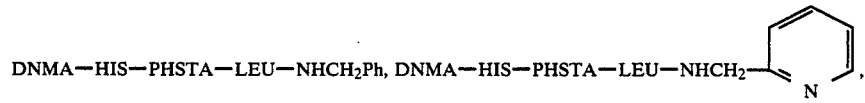,

DNMA—LEU—STA—NHCH₂CH(OH)CH₂SCH(CH₃)₂, DNMA—LEU—STA—NHCH₂CH(OH)CH₂SOCH(CH₃)₂,
DNMA—LEU—STA—NHCH₂CH(OH)CH₂SO₂CH(CH₃)₂, DNMA—HIS—STA—NHCH₂CH(OH)CH₂SOCH(CH₃)₂,

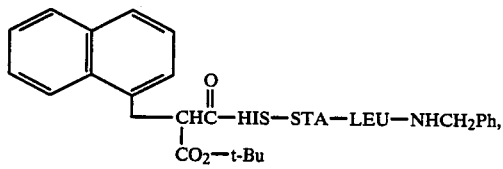
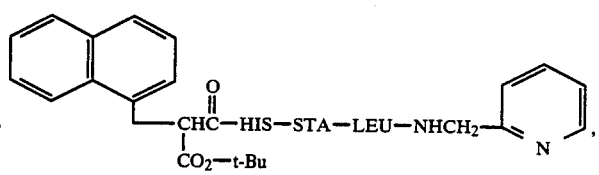

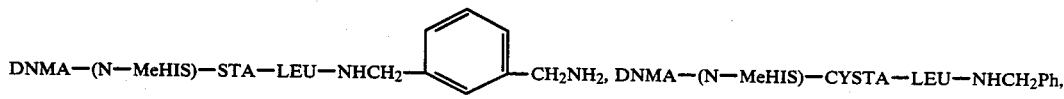

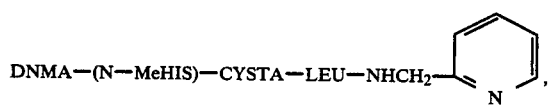

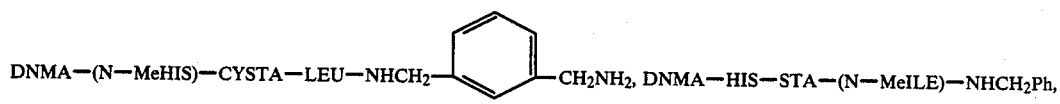

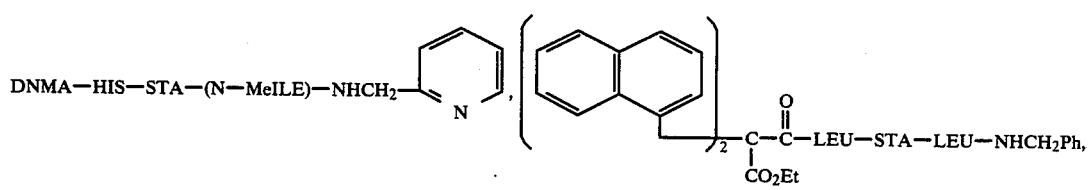

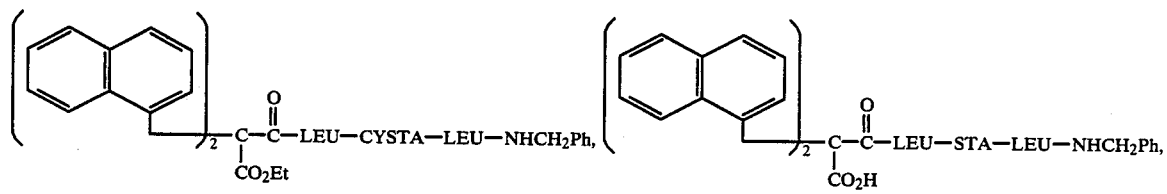

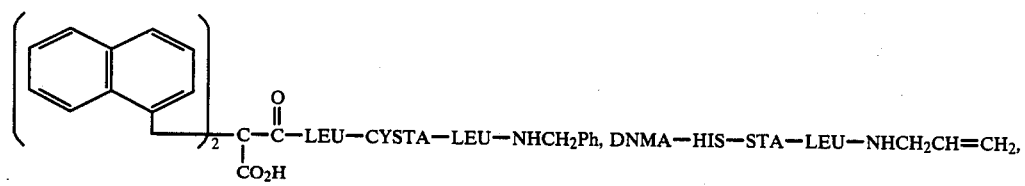

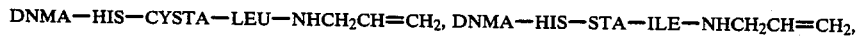

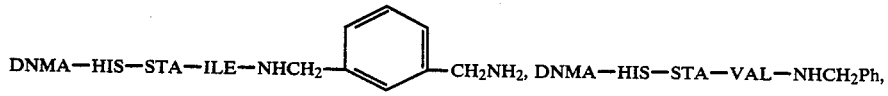

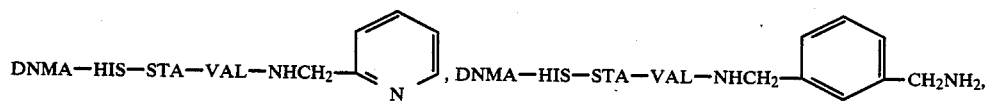

The compounds of the present invention include solvates, hydrates and pharmaceutically acceptable acid addition salts of the basic compounds of formula I above.

The term pharmaceutically acceptable acid addition salt is intended to mean a relatively nontoxic acid addition salt either from inorganic or organic acids such as, for example, hydrochloric, hydrobromic, hydroiodic, sulfuric, phosphoric, acetic, citric, oxalic, malonic, salicyclic, malic, benzoic, gluconic, fumaric, succinic, ascorbic, maleic, tartaric, methanesulfonic and the like. The salts are prepared by contacting the free base form with a sufficient amount of the desired acid to produce a salt in the conventional manner. The free base forms may be regenerated by treating the salt form with a base.

The modified peptides of the present invention possess one or more chiral centers and each center may exist in the R(D) or S(L) configuration. The present invention includes all enantiomeric and epimeric forms as well as the appropriate mixtures thereof.

Some of the above novel peptides may be prepared in accordance with well-known procedures for preparing peptides from their constituent amino acids. Other of the novel peptides of the present invention are prepared by a step-wise procedure or by a fragment coupling procedure depending upon the particular final product desired.

The following schemes illustrate novel methods of preparing certain peptides of the present invention.

SCHEME I

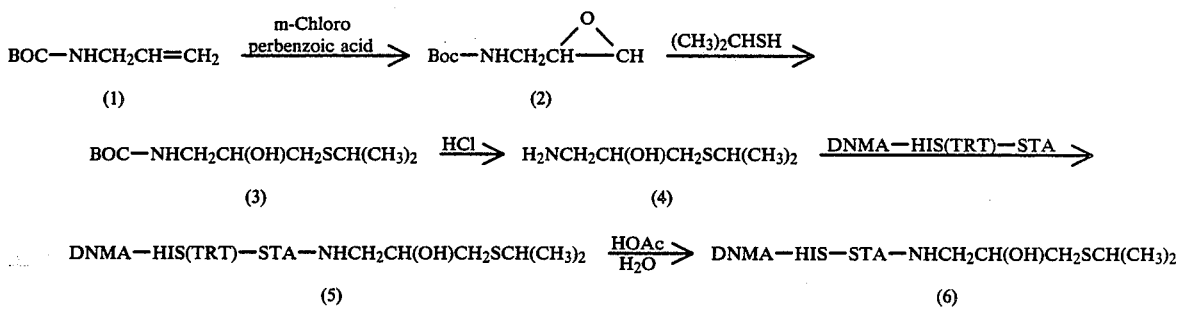

According to Scheme I above, a BOC-protected, NH-substituted-1-alkene (1), for example, an allyl amine is reacted with an epoxidizing agent to form the corresponding protected epoxide (2). The epoxide is reacted with a mercaptan forming a protected thioether (3). The thioether is then reacted with HCl to remove the protecting group forming the corresponding compound (4) with a free amino terminus. The amine is reacted with an amino acid or a peptide, having a free terminal carboxylic acid, for example, DNMA—HIS(TRT)—STA, to form the corresponding peptide having a thio-containing amide moiety (5) which is then reacted with aqueous acetic acid to remove the TRT group forming the desired compound (6), of formula I of the instant invention. This may be converted, if desired, to a pharmaceutically acceptable acid addition salt.

Epoxidizing agents useful in the reaction are m-chloroperbenzoic acid, perbenzoic acid, and perphthalic acid. The preferred agent is m-chloroperbenzoic acid.

The reaction takes place in an inert solvent such as methylene chloride, tetrahydrofuran, chloroform, dioxane, or ethylacetate. The preferred solvent is methylene chloride.

Among the mercaptans possible in this sequence are any of the alkyl mercaptans, aralkyl mercaptans, or aryl mercaptans. The preferred mercaptan is isopropyl mercaptan.

The protecting group is removed with a strong acid such as trifluoroacetic, HCl, or HBr. Preferably HCl is used.

Removal of TRT is accomplished with aqueous acetic acid, dilute HCl, or dilute $H_2SO_4$. Preferably this is done with aqueous acetic acid.

The epoxidation reaction is mildly exothermic and can be carried out at temperatures between 0° C. and 25° C. The preferred reaction temperature is about room temperature.

The reaction time varies from 4 to 48 hours. Preferably it is about 24 hours.

The term protecting group refers to those groups intended to protect the N-terminus against undesirable reactions during synthetic procedures or to increase the solubility of the desired final compounds and includes but is not limited to Z and BOC.

The term lower alkyl refers to straight or branched chain alkyl radicals containing from 1 to 6 carbon atoms including but not limited to methyl, ethyl, n-propyl, isopropyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl and the like.

SCHEME II

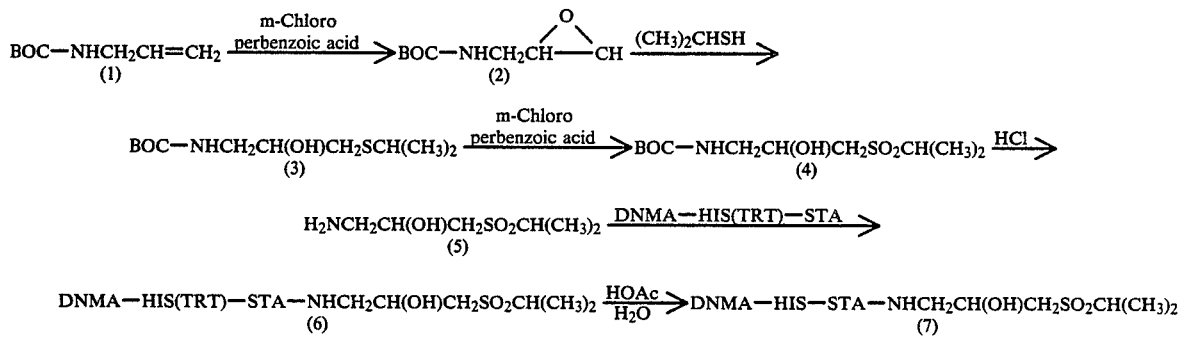

Alternatively certain compounds of the present invention having a sulfone linkage can be made according to Scheme II above. The thioether (3) of Scheme I is oxidized to form the corresponding sulfone by reaction with a peracid. The protected sulfone (4) above is reacted with HCl to produce a compound with the free amino terminus (5). This compound is reacted with DNMA—HIS(TRT)—STA to form a sulfone-containing peptide (6). This is reacted with aqueous acetic acid to form peptides (7) of formula I of the instant invention. These can be converted to the pharmaceutically acceptable acid addition salt.

The strategy of peptide chain assembly and selection and removal of protecting groups is discussed in Chapter 1, "The Peptide Bond," in "The Peptides. Analysis, Synthesis, Biology," E. Gross and J. Meienhofer, Eds., Academic Press, New York, NY, 1979, pp. 42–44.

The DCC/HOBT method of coupling is well known to those skilled in the art and is discussed in Chapter 5, "The Carbodiimide Method" by D. H. Rich and J. Singh in "The Peptides. Analysis, Synthesis, Biology," E. Gross and J. Meienhofer, Eds., Academic Press, New York, NY, 1979, pp. 42–44.

Peptide coupling depends on activating the carboxyl group of the protected amino acid prior to condensing it with another peptide containing a free amino terminus. In addition to the DCC coupling method described above, other methods of activating the carboxyl group of a protected amino acid include:

(1) The azide method—described in Chapter 4 of the above reference.
(2) The mixed anhydride method—described in Chapter 6 of the above reference.
(3) The active ester method—described in Chapter 3 of the above reference.

The compounds of the present invention are useful for treating renin-associated hypertension and hyperaldosteronism. They are also useful as diagnostic tools for determining the presence of renin-associated hypertension of hyperaldosteronism.

Pharmaceutical compositions which comprise an effective amount of the compound in combination with a pharmaceutically acceptable carrier are part of the present invention. An important aspect of the present invention is a method of treating renin associated hypertension in a mammal which comprises administering a pharmaceutical composition containing an effective amount of a compound of the invention in combination with a pharmaceutically acceptable carrier to the mammal.

Another equally important aspect of the present invention is a method of treating hyperaldosteronism in a mammal which comprises administering a pharmaceutical composition containing an effective amount of a compound of the invention in combination with a pharmaceutically acceptable carrier to the mammal.

The effectiveness of the aforementioned compound is determined by a test for in vitro renin inhibitory activity. This activity is determined by a standard radioimmunoassay for angiotensin I. In this assay the enzyme, renin, incubated for two hours at 37° C. in the presence of a substrate, angiotensinogen, generates the product, angiotensin I. Test compounds are added to the incubation mixture. Relative activity is reported as the $IC_{50}$, which is the molar concentration of test compound causing a 50% inhibition of the renin activity.

| Example | Activity $IC_{50}$ (M) |
|---|---|
| DNMA—HIS—STA—LEU—NHCH$_2$Ph | $1.3 \times 10^{-8}$ |
| 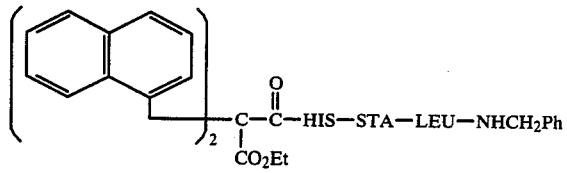 | $5.6 \times 10^{-7}$ |
| 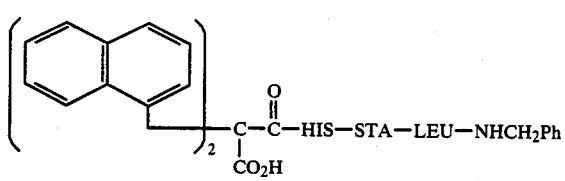 | $4.3 \times 10^{-7}$ |
| 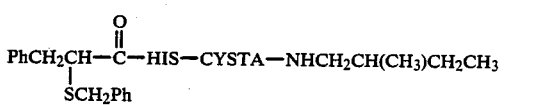 | $1.7 \times 10^{-6}$ |
| 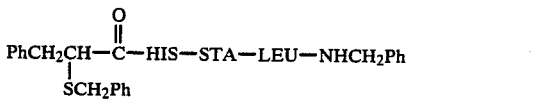 | $2.2 \times 10^{-6}$ |
| 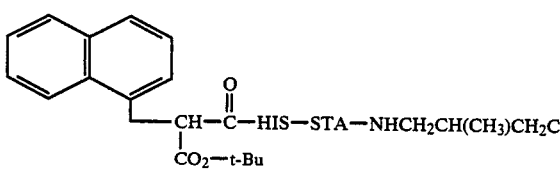 | $3.2 \times 10^{-6}$ |
| DNMA—HIS—STA—NHCH$_2$CH=CH$_2$ | $1.9 \times 10^{-7}$ |
| DNMA—HIS—STA—NHCH$_2$CH(OH)CH$_2$SCH(CH$_3$)$_2$ | $2.2 \times 10^{-7}$ |

| Example | Activity IC$_{50}$ (M) |
|---|---|
| DNMA—HIS—STA—NHCH$_2$CH(OH)CH$_2$SO$_2$CH(CH$_3$)$_2$ | 8.2 × 10$^{-8}$ |

The effectiveness of the aforementioned compounds in vivo is determined by their effect on lowering renin maintained blood pressure in the anesthetized, vagotomized, ganglionic-blocked rat.

After the blood pressure has stabilized, 1.25 mg/kg IV mecamylamine is added to produce ganglionic blockade. Hog renin is then infused to bring the blood pressure to a level observed before vagotomy and ganglionic blockade. Test compound is then administered IV and the drop in blood pressure is noted.

| Compound | Percent Decrease of Blood Pressure |
|---|---|
| DNMA—HIS—STA—LEU—NHCH$_2$Ph | 65% |

The compound was administered at as dose of 1 mg/kg.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents. It can also be encapsulting material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

The compounds of the present invention may be administered orally, buccally, parenterally, by inhalation spray, rectally or topically in dosage unit formulations containing conventional nontoxic pharmaceutically acceptable carriers, adjuvants and vehicles as desired. The term parenteral as used herein includes subcutaneous injections, intravenous, intramuscular, intrasternal injection or infusion techniques.

For preparing suppositories, a low melting wax such as a mixture of fatty acid glycerides or cocoa butter is first melted, and the active ingredient is dispersed homogeneously therein by stirring. The molten homogeneous mixture is then poured into convenient sized molds, allowed to cool, and thereby solidify.

Liquid form preparations include solutions, suspensions, and emulsions. As an example may be mentioned water or water/propylene glycol solutions for parenteral injection. Liquid preparations can also be formulated in solution in aqueous polyethyleneglycol solution. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient. The compositions can, if desired, also contain other compatible therapeutic agents.

In therapeutic use as renin inhibitors, the mammalian dosage range for a 70 kg subject is from 1 to 1500 mg of body weight per day or preferably 25 to 750 mg of body weight per day optionally in divided portions. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following Examples are provided to enable one skilled in the art to practice the present invention. These examples are not intended in any way to limit the scope of the invention but are illustrative thereof.

EXAMPLE 1

DNMA—HIS—STA—LEU—NHCH$_2$Ph

DNMA—HIS(TRT)—STA—LEU—NHCH$_2$Ph (1.30 g, 1.20 mmole) was dissolved in 80 ml of 80% HOAc and heated on a steam bath for five minutes. The solution was allowed to cool to 25° over one hour, after which the solvent was removed in vacuo. The residue was dissolved in Et$_2$O to which was added brine, giving an oily precipitate of the crude product. The ether phase was separated, and the aqueous suspension of the oil was washed with ethyl ether to remove residual trityl alcohol. The aqueous and oil phases were then adjusted to pH 12 by addition of 1N NaOH, and were exhaustively extracted with EtOAc. The organic phase was washed with brine, dried over MgSO$_4$, filtered, and the filter cake washed with CH$_2$Cl$_2$. The filtrates were combined and stripped to an oil, which was taken up into a minimal amount of EtOAc. A solid was precipitated by addition of Et$_2$O, which was filtered, washed with Et$_2$O and dried to a white solid, 0.64 g. NMR, IR, and mass spectral analysis confirmed the structure of the product.

Calcd. for C$_{51}$H$_{60}$N$_6$O$_5$.0.06CHCl$_3$ (MW 844.54): C, 72.62; H, 7.17; N, 9.95. Found C, 72.30; H, 7.18; N, 9.97.

EXAMPLE 2

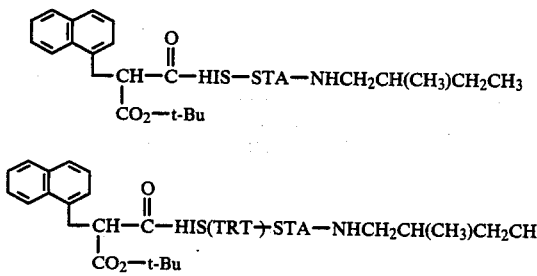

(3.53 g, 3.88 mmole) was dissolved in 25 ml of 80% HOAc and heated on a steam bath for two minutes. The solvent was removed in vacuo and the residue dissolved in EtOAc. The EtOAc solution was washed with 1N NaOH, then brine. After drying over MgSO$_4$ and filtering, the filtrate was reduced to one-fourth volume in vacuo giving a gel. Diluting with Et$_2$O gave 2.41 g of the product as a white solid. IR, NMR, and mass spectral analysis confirmed the structure.

EXAMPLE 3

DNMA—HIS—STA—NHCH$_2$CH(OH)CH$_2$SCH(CH$_3$)$_2$

A solution of 0.5 g (0.5 mmole) of DNMA—HIS(TRT)—STA—NHCH$_2$CH(OH)CH$_2$SCH(CH$_3$)$_2$ in 15 ml of 80% HOAc was heated on a steam bath for ten minutes, then allowed to cool to room temperature. The solvent was removed in vacuo, water added, and the solution again stripped in vacuo. The residue was taken up in EtOAc, washed with brine, dried over MgSO$_4$, and filtered. Addition of Et$_2$O to the filtrate gave the crude product as a solid. Chromatography on silica gel, eluting with 2% MeOH in CHCl$_3$ gave 0.22 g of the product as a white foam. NMR and mass spectral analysis confirmed the structure.

Calcd. for C$_{44}$H$_{55}$N$_5$O$_5$S.0.16CHCl$_3$: C, 67.50; H, 7.07; N, 8.91. Found C, 67.29; H, 7.02; N, 8.83.

EXAMPLE 4

DNMA—HIS—STA—NHCH$_2$CH(OH)CH$_2$SO$_2$CH(CH$_3$)$_2$

DNMA—HIS(TRT)—STA—NHCH$_2$CH(OH)CH$_2$SO$_2$CH(CH$_3$)$_2$ (0.63 g, 0.61 mmole) was heated on a steam bath for five minutes in 15 ml 90% HOAc. After cooling to 25° over thirty minutes, the solvent was stripped off and the residue was taken up into H$_2$O. The mixture was stripped, taken up into EtOAc, and dried over MgSO$_4$. The solution was filtered and reduced in volume. Addition of Et$_2$O precipitated a solid which was collected and dried to give 0.37 g of product. NMR and mass spectral analysis confirmed the structure.

INTERMEDIATES FOR EXAMPLE 1

BOC—STA—LEU—NHCH$_2$Ph 1.80 g LEU-NHCH$_2$Ph.HCl [Japan 83/59952], 2.27 g BOC—STA (U.S. Pat. No. 4,397,786) and 1.04 g 1-hydroxybenzotriazole-hydrate were dissolved in 125 ml dichloromethane and cooled to 0°. 1.07 ml of Et$_3$N was then added. A cold solution of 1.59 g dicyclohexylcarbodiimide in 20 ml dichloromethane was added, followed by the addition of 50 ml cold dimethylformamide. The mixture was stirred at 9° for two hours, followed by 12° overnight. The mixture was then filtered, stripped to a paste, and resuspended in ethyl acetate. The suspension was filtered, the filtrate washed with 1N citric acid, saturated sodium chloride solution, saturated sodium bicarbonate solution, and saturated sodium chloride solution, and dried over anhydrous magnesium sulfate. The suspension was filtered and stripped to a white foam 3.77 g, which was crystallized from ethyl ether and hexane giving a white solid, 3.41 g (92% yield), mp 89°-92°. Spectral and elemental analysis confirmed the anticipated structure. $[\alpha]_D^{23} = -34.2°$ (C, 1.06, MeOH).

STA—LEU—NHCH$_2$Ph.HCl 2.77 g BOC—STA—LEU—NHCH$_2$Ph was dissolved in 100 ml dichloromethane, which was then saturated with anhydrous hydrogen chloride gas. After stirring at 25° for one hour, the solvent was removed in vacuo, and the residue resuspended in dichloromethane, giving a crystalline solid. The suspension was diluted with ethyl ether, filtered, and the solid dried in vacuo, 2.24 g, 93% yield. Spectral and elemental analysis confirmed the structure. $[\alpha]_D^{23} = -19.1°$ (C, 1.06, MeOH).

Z—HIS(TRT)—OCH$_3$

Z—HIS—OCH$_3$ [J. Chem. Soc., Perkin I, 2261 (1979)] (70 g) was dissolved in dichloromethane (500 ml) and cooled to 0°. Triethyl amine (32 ml) and then trityl chloride (64.3 g) were added. The mixture was washed with sodium bicarbonate and brine, dried over sodium sulfate, filtered, and evaporated. The residue was recrystallized from ethyl acetate to give 100 g of product.

Z—HIS(TRT)

A—HIS(TRT)—OCH$_3$ (30 g) was dissolved in 300 ml of dioxane and cooled to 0°. Sodium hydroxide (2.7 g) in 80 ml of water was added. The mixture was stirred for one hour and then acidified with 1N citric acid to pH 2. The mixture was extracted with ethyl acetate. The organic phase was washed with brine, dried over sodium sulfate, filtered, and evaporated to give 27 g of product.

Z—HIS(TRT)—STA—LEU—NHCH$_2$Ph

Z—HIS(TRT) (4.65 g, 8.75 mmole) and HOBT.H$_2$O (1.24 g, 9.18 mmole) were dissolved in 5 ml DMSO, diluted to 150 ml with CH$_2$Cl$_2$, and cooled to −5°. A solution of DCC (1.9 g, 9.18 mmole) in 30 ml CH$_2$Cl$_2$ was added. A solution of STA—LEU—NHCH$_2$Ph.HCl (3.62 g, 8.75 mmole) and Et$_3$N (1.28 ml, 9.18 mmole) in 50 ml cold CH$_2$Cl$_2$ was added, and the mixture was stirred at −5°, and allowed to warm to 25° for two days. The solids were then filtered off, and the filtrate was stripped to an oil. The oil was suspended in EtOAc, washed with brine, 1N citric acid, brine, saturated NaHCO$_3$ solution, and brine. The organic phase was dried over MgSO$_4$, filtered, and stripped to an oil. The oil was dissolved in EtOAc and a precipitate was filtered off. The filtrate was diluted with Et$_2$O and stripped to give 8.17 g of the product as a foam. NMR and mass spectral analysis confirmed the structure. The product was sufficiently pure for use in the following steps.

HIS(TRT)—STA—LEU—NHCH$_2$Ph

Z—HIS(TRT)—STA—LEU—NHCH$_2$Ph (8.0 g, 8.98 mmole) was dissolved in 200 ml MeOH to which was added 0.50 g 20% Pd on charcoal catalyst. The suspension was purged with H$_2$ gas over 3.5 hours, filtered, and stripped to a glass, 7.31 g. The crude material was chromatographed on silica gel, eluting with a gradient of 2 to 5% MeOH in CHCl$_3$, giving a white foam, 5.74 g. NMR and mass spectral analysis confirmed the structure of the product.

DNMA—HIS(TRT)—STA—LEU—NHCH$_2$Ph

Di(1-naphthylmethyl)acetic acid (0.65 g, 1.91 mmole) and HOBT.H$_2$O (0.271 g, 2.0 mmole) were dissolved in 4 ml DMF, diluted to 30 ml with CH$_2$Cl$_2$ and cooled to 0°. DCC (0.414 g, 2.0 mmole) was added, followed by a solution of HIS(TRT)—STA—LEU—NHCH$_2$Ph (1.52 g, 1.91 mmole) in 20 ml CH$_2$Cl$_2$. The mixture was stirred and allowed to warm to 25° overnight. The mixture was filtered, and the solvent removed in vacuo. The residue was dissolved in EtOAc and washed with 1N citric acid, brine, saturated NaHCO$_3$ solution, and brine. The organic phase was dried over MgSO$_4$, filtered, and stripped to a foam, 2.05 g. The foam was chromatographed on silica gel, eluting with a gradient of 0 to 2% MeOH in CHCl$_3$. Combining the appropriate fractions using Et$_2$O gave 1.47 g of the product as a white foam. NMR, IR, and mass spectral analysis confirmed the structure of the product.

INTERMEDIATES FOR EXAMPLE 2

BOC—STA—NHCH$_2$CH(CH$_3$)CH$_2$CH$_3$

BOC—STA (27.53 g, 0.1 mole, U.S. Pat. No. 4,397,786) and HOBT.H$_2$O (14.2 g, 0.105 mole) were dissolved in 40 ml DMF. 300 ml CH$_2$Cl$_2$ was added, and the mixture was cooled to 0°. A solution of DCC (21.66 g, 0.105 mole) in 50 ml CH$_2$Cl$_2$ was added, followed by S-2-methylbutylamine (12 ml, 0.1 mole). After stirring at 0° for two hours, the mixture was allowed to warm to 25° over 1.5 hours. The mixture was filtered and the solvent was removed in vacuo. The residue was dissolved in EtOAc, which was washed with 1N citric acid, brine, saturated NaHCO$_3$ solution, and brine. The organic phase was dried over MgSO$_4$, filtered, and stripped to a gum, 36.90 g. The gum was dissolved in Et$_2$O and treated with charcoal to remove colored impurities. The suspension was filtered and stripped to a gum, 35.2 g, which was suitable for use in the following procedure without further purification.

STA—NHCH$_2$CH(CH$_3$)CH$_2$CH$_3$.HCl

BOC—STA—NHCH$_2$CH(CH$_3$)CH$_2$CH$_3$ (34.4 g, 0.1 mole) was dissolved in 250 CH$_2$Cl$_2$ and the solution was purged occasionally with anhydrous HCl gas over three hours. A solid precipitated from solution which was filtered, washed with CH$_2$Cl$_2$, and dried at 40° in vacuo to a hygroscopic solid, 21 g. The solid was triturated with a mixture of CH$_2$Cl$_2$/Et$_2$O, filtered, and dried at 40° in vacuo to a white solid, 19.34 g. Spectral analysis confirmed the structure.

Z—HIS(TRT)—STA—NHCH$_2$CH(CH$_3$)CH$_2$CH$_3$

Z—HIS(TRT) (4.37 g, 8.22 mmole) and HOBT.H$_2$O (1.17 g, 8.63 mmole) were dissolved in 10 ml DMF, diluted to 50 ml with CH$_2$Cl$_2$, and cooled to −2°. A solution of DCC (1.78 g, 8.63 mmole) in 20 ml CH$_2$Cl$_2$ was added, followed by a solution of STA—NHCH$_2$CH(CH$_3$)CH$_2$CH$_3$.HCl (1.72 g, 6.12 mmole) in a mixture of 10 ml DMF, 10 ml CH$_2$Cl$_2$ and Et$_3$N (1.20 ml, 8.63 mmole). The mixture was stirred at 0° and allowed to warm to 25° overnight. The mixture was filtered, stripped to an oil, and the residue dissolved in a mixture of EtOAc and Et$_2$O. The solution was washed with 1N citric acid, brine, saturated NaHCO$_3$ solution, and brine, followed by drying over NgSO$_4$, filtration, and stripping to a foam, 5.62 g. The foam was chromatographed on silica gel, eluting with a gradient of 0 to 3% MeOH in CHCl$_3$. The product was recovered as a foam, 3.15 g. IR, NMR, and mass spectral analysis confirmed the structure.

HIS(TRT)—STA—NHCH$_2$CH(CH$_3$)CH$_2$CH$_3$

A solution of Z—HIS(TRT)—STA—NHCH$_2$CH(CH$_3$)CH$_2$CH$_3$ (2.91 g, 3.84 mmole) in 80 ml MeOH was treated with 20% Pd on charcoal (0.13 g) and was then purged with hydrogen gas for seven hours. The mixture was filtered, stripped to an oil, redissolved in Et$_2$O/hexane and stripped to a foam, 2.39 g. The material was sufficiently pure to use in the following step. IR, NMR, and mass spectral analysis confirmed the structure.

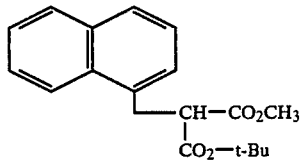

NaH (10.46 g, 50% emulsion in oil, 0.218 mole) was washed with dry THF to remove the oil. The residue was suspended in 500 ml THF to which was added a solution of t-butyl methyl malonate (34.5 g, 0.198 mole) in 50 ml THF. A vigorous reaction ensued, giving a paste-like precipitate. After heating at reflux for thirty minutes, the mixture was cooled to 35° and 1-chloromethylnaphthalene (35.0 g, 0.198 mole) was added. The mixture was stirred at 40° overnight, stripped to a paste, and the residue taken up in EtOAc. The suspension was washed with 1N citric acid, brine, saturated NaHCO3, brine, and then dried over MgSO4. The solution was filtered and stripped to a yellow oil, 58.84 g. The product was used in the following step without further purification.

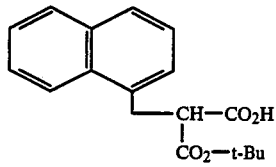

A solution of 61 g (0.194 mole) of crude

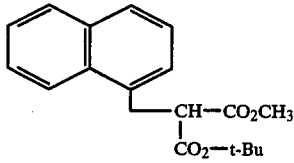

in 250 ml of MeOH was treated with 40 g of 50% NaOH solution and stirred for five hours forming a paste. The mixture was filtered, washed with MeOH, and the filtrate stripped to a paste. The paste was taken up in H2O and washed with Et2O. The pH was adjusted to 2.0 with dilute HCl and the mixture extracted with Et2O. The Et2O was washed with brine, dried over MgSO4, filtered, and stripped to an oil, 22.19 g. This was dissolved in CHCl3 and a crystalline solid filtered off. Removal of the solvent under reduced pressure gave 13.8 g of a syrup. Chromatography on silica gel, eluting with EtOAc/hexane (1:1) gave the product as a foam. IR, NMR, and mass spectral analysis confirmed the structure.

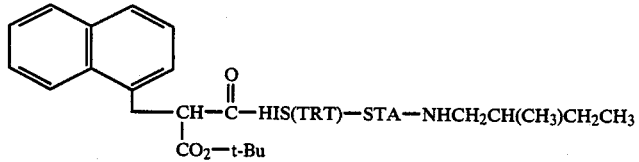

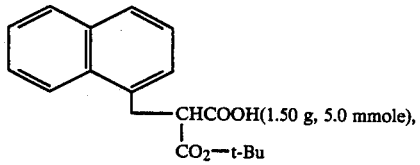

HIS(TRT)—STA—NHCH2CH(CH3)CH2CH3 (3.12 g, 5.0 mmole) and HOBT.H2O (0.21 g, 5.25 mmole) were dissolved in 80 ml DMF and cooled to 0°. DCC (1.08 g, 5.25 mmole) was added, and the mixture was stirred overnight at 25°. The mixture was filtered and stripped to a syrup in vacuo, which was taken up into EtOAc. The solution was washed with 1N citric acid, brine, saturated NaHCO3 solution, and brine. The solution was dried over MgSO4, filtered, and stripped to a foam, 4.85 g. The foam was chromatographed on silica gel, eluting with 2% MeOH in EtOAc. The product was recovered as a foam, 3.50 g. Mass spectral analysis confirmed the structure.

INTERMEDIATES FOR EXAMPLE 3

BOC—NHCH2CH=CH2

Di-t-butyldicarbonate (43.65 g, 0.2 mole) was dissolved in 250 ml CH2Cl2, to which was added allyl amine (15.0 ml, 0.2 mole) in a dropwise manner. After stirring overnight, the mixture was stripped to an oil, dissolved in EtOAc, and washed with 1N citric acid, brine, saturated NaHCO3 solution, and brine. The solution was dried over MgSO4, filtered, and stripped to an oil which crystallized, 30.02 g. NMR confirmed the structure.

A solution of 21.72 g (0.138 mole) of BOC—allylamine in 250 ml of CH2Cl2 was treated with 28 g (0.138 mole) of m-chloroperbenzoic acid causing a mild exotherm. After stirring overnight the mixture was filtered and the filtrate washed with 10% sodium sulfite solution, 1N citric acid, saturated NaHCO3, and brine. Drying over MgSO4, filtering, and removing the solvent under reduced pressure left 25.0 g of the crude product as an oil. Chromatography on silica gel, eluting with 75/25 hexane/EtOAc gave 17.1 g of a clear oil. NMR, IR, and mass spectral analysis confirmed the structure.

BOC—NHCH2CH(OH)CH2SCH(CH3)2

NaH (3.18 g, 50% emulsion in oil, 0.066 mole) was washed free of oil with dry THF and was suspended in 100 ml DMF. Isopropyl mercaptan (14.0 ml, 0.151 mole) was added slowly. Solution occurred after stirring thirty minutes. The mixture was cooled to 25° and

(11.5 g, 0.066 mole) was added as a solution in 30 ml THF. The mixture was stirred overnight and the pH was then adjusted to 7 with 12% HCl. The solvent was removed in vacuo. The residue was taken up in EtOAc, washed with brine, 1N citric acid, brine, saturated NaHCO₃ solution, and brine. The EtOAc solution was dried over MgSO₄, filtered, and stripped to an oil, 15.84 g. The product was chromatographed on silica gel, eluting with 50/50 hexane/EtOAc, giving an oil, 14.85 g. IR, NMR, and mass spectral analysis confirmed the structure.

H₂N—CH₂CH(OH)CH₂SCH(CH₃)₂.HCl

BOC—NHCH₂CH(OH)CH₂SCH(CH₃)₂ (3.74 g, 0.015 mole) was dissolved in 75 ml CH₂CL₂ and occasionally purged with HCl gas over two hours. The solvent was removed in vacuo, and the residue was triturated with Et₂O. The solvent was decanted and the residue was stripped to a foam, 2.83 g. IR, NMR, and mass spectral analysis confirmed the structure.

BOC—STA—OCH₃

BOC—STA (35.9 g, 0.13 mole, U.S. Pat. No. 4,397,786) was dissolved in 1 l EtOAc. An ethereal solution of diazomethane (prepared from 52 g p-tolyl-sulfonylmethylnitrosamide per *Organic Synthesis*, Collective Volume 4, pp. 251-3) was added to the EtOAc solution until a slight yellow color persisted. After stirring at 25° for two hours, HOAc was added until the yellow color disappeared. After stirring thirty minutes, the solvent was removed in vacuo giving the product as a crystalline solid, 40.1 g.

STA—OCH₃.HCl

BOC—STA—OCH₃ (37.4 g, 0.13 mole) was dissolved in 600 ml CH₂Cl₂ which was occasionally purged with anhydrous HCl gas over four hours. When thin layer chromatography indicated complete consumption of the starting material, the solvent was removed in vacuo and the residue resuspended in CH₂Cl₂/Et₂O, which gave a crystalline solid, 30.8 g. The material was sufficiently pure for use in the following steps.

Z—HIS(TRT)—STA—OCH₃

Z—HIS(TRT) (28.97 g, 0.0545 mole) and HOBT.H₂O (7.73 g, 0.0572 mole) were dissolved in 250 ml DMF and cooled to 0°. STA—OCH₃.HCl (12.3 g, 0.0545 mole) was added as a solution in 75 ml DMF containing Et₃N (7.97 ml, 0.0572 mole). To the mixture was added a cold solution of DCC (11.81 g, 0.0572 mole) in 50 ml DMF. After warming from 0° to 25° over five hours, the mixture was refrigerated overnight at 4°. The mixture was filtered, stripped to an oil, and taken up into EtOAc. The solution was washed with 1N citric acid, brine, saturated NaHCO₃ solution, and brine. The solution was dried over MgSO₄, filtered, and stripped to an oil. The oil was chromatographed on silica gel, eluting with a gradient of 0 to 5% MeOH in CHCl₃, giving the product as a white solid, 30.7 g.

HIS(TRT)—STA—OCH₃

Z—HIS(TRT)—STA—OCH₃ (10.0 g, 0.0142 mole) and 20% Pd on charcoal catalyst (0.5 g) were added to 200 ml MeOH, which was then purged with hydrogen gas over five hours. The mixture was filtered and stripped to a foam, 8.03 g. IR, NMR, and mass spectral analysis confirmed the structure.

DNMA—HIS(TRT)—STA—OCH₃

Di-(1-naphthylmethyl)acetic acid (2.63 g, 7.73 mmole), HOBT.H₂O (0.834 g, 8.25 mmole), HIS(TRT)—STA—OCH₃ (4.32 g, 7.5 mmole), and DCC (1.70 g, 8.25 mmole) were dissolved in 100 ml DMF and stirred at 25° for sixteen hours. The mixture was filtered, stripped to an oil, and the residue was taken up into EtOAc. The solution was washed with 1N citric acid, saturated NaHCO₃ solution, and brine, followed by drying over MgSO₄, filtering, and stripping to a yellow foam, 7.19 g. The foam was chromatographed on silica gel eluting with EtOAc, and giving a foam, 4.60 g. NMR and mass spectral analysis confirmed structure.

DNMA—HIS(TRT)—STA

DNMA—HIS(TRT)—STA—OCH₃ (3.1 g, 3.44 mmole) and NaOH (0.20 g, 5.16 mmole) were dissolved in a mixture of 50 ml dioxane and 56 ml H₂O. After five hours, the pH was adjusted to 7 with 1N HCl. The solvent was removed in vacuo and the residue was taken up into EtOAc. The solution was washed with 1N citric acid and brine, dried over MgSO₄, filtered, and stripped to reduced volume. Addition of Et₂O gave a precipitate which was filtered off and dried to give a solid, 2.15 g. The structure of the product was confirmed by mass spectral analysis.

DNMA—HIS(TRT)—STA—NHCH₂CH(OH)CH₂SCH(CH₃)₂

DNMA—HIS(TRT)—STA (0.65 g, 0.74 mmole) and HOBT.H₂O (0.105 g, 0.78 mmole) were dissolved in 10 ml DMF. H₂N—CH₂CH(OH)CH₂SCH(CH₃)₂.HCl (0.138 g, 0.74 mmole) was added as a solution in a mixture of 5 ml DMF and Et₃N (0.109 ml, 0.78 mmole). DCC (0.16 g, 0.78 mmole) was added, and the mixture was stirred overnight. The mixture was filtered, stripped, and the residue was taken up into EtOAc. The solution was washed with 1N citric acid, brine, saturated NaHCO₃ solution, and brine. The solution was dried over MgSO₄, filtered, and stripped to a foam, 0.81 g. The foam was chromatographed on silica gel, eluting with 2% MeOH in CHCl₃, and giving the product as a white foam, 0.50 g. Mass spectral analysis confirmed the structure.

INTERMEDIATES FOR EXAMPLE 4

BOC—NHCH₂CH(OH)CH₂SO₂CH(CH₃)₂

BOC—NHCH₂CH(OH)CH₂SCH(CH₃)₂ (3.74 g, 0.015 mole) and m-chloroperbenzoic acid (7.76 g, 0.045 mole) were dissolved with cooling in 100 ml CH₂Cl₂. The mixture was stirred at 25° overnight, and stripped to a solid. The solid was dissolved in EtOAc, washed with 10% sodium sulfite solution, saturated NaHCO₃ solution, and brine. The solution was dried over MgSO₄, filtered, and stripped to an oil, 4.15 g. The oil was chromatographed on silica gel eluting with 50/50 hexane/EtOAc, and giving the product as an oil, 3.66 g. NMR and mass spectral analysis confirmed the structure.

H₂N—CH₂CH(OH)CH₂SO₂CH(CH₃)₂.HCl

BOC—NHCH₂CH(OH)CH₂SO₂CH(CH₃)₂ (3.19 g, 11.35 mmole) was dissolved in 75 ml CH₂Cl₂ and purged with HCl gas over two hours. The mixture was stripped, triturated with ethyl ether, and filtered. The solid was washed with ethyl ether and dried giving 2.21 g of product.

DNMA—HIS(TRT)—STA—NHCH₂CH(OH)CH₂SO₂CH(CH₃)₂

DNMA—HIS(TRT)—STA (0.59 g, 0.67 mmole) and HOBT.H₂O (0.095 g, 0.71 mmole) were dissolved in 10 ml DMF. A solution of H₂N—CH₂CH(OH)CH₂SO₂CH(CH₃)₂.HCl (0.146 g, 0.67 mmole) in 10 ml DMF and Et₃N (0.11 ml, 0.71 mmole) was added, followed by DCC (0.15 g, 0.71 mmole). The mixture was stirred at 25° overnight, stripped, and the residue taken up into EtOAc. The suspension was washed with 1N citric acid, brine, saturated NaHCO₃ solution, and brine. The solution was dried over MgSO₄, filtered, and stripped to a foam, 0.81 g. The foam was chromatographed on silica gel eluting with 2% MeOH in CHCl₃, and giving the product as a white foam, 0.63 g. Mass spectral analysis confirmed the structure.

We claim:
1. A peptide of the formula

ACYL—X—Y—W—U    (I)

or a pharmaceutically acceptable acid addition salt thereof, wherein
ACYL is DNMA,

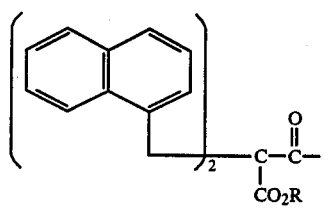

wherein
R is hydrogen or a straight or branched lower alkyl of from one to six carbon atoms,

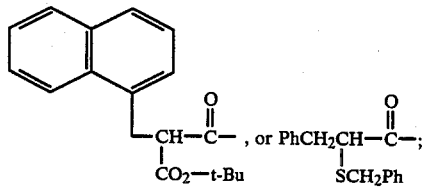

X is HIS, HOMOHIS, PHE, HOMOPHE, ILE, LEU, NLE, N—MeHIS, N—MeLEU, or

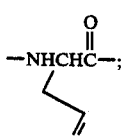

Y is STA, CYSTA, or PHSTA;
W is LEU, ILE, N—MeLEU, N—MeILE, VAL or absent with the proviso that, when ACYL is DNMA, W is present; and
U is —NHCH₂CH(CH₃)CH₂CH₃, —NHCH₂Ph,—NHCH₂CH(OH)CH₂SCH(CH₃)₂, —NHCH₂CH(OH)CH₂SOCH(CH₃)₂, —NHCH₂CH(OH)CH₂SO₂CH(CH₃)₂,

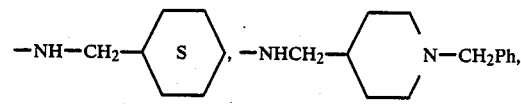

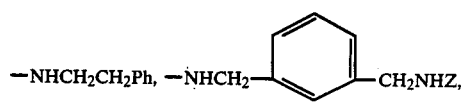

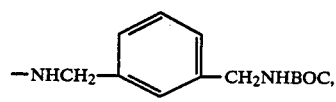

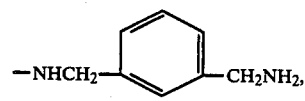

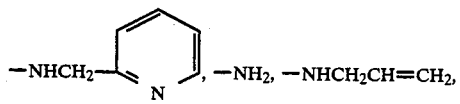

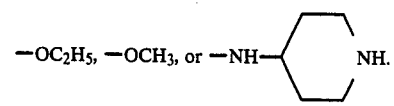

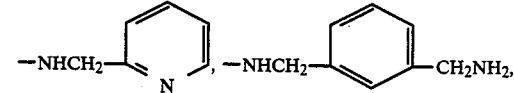

2. A peptide according to claim 1 wherein U is —NHCH₂Ph,

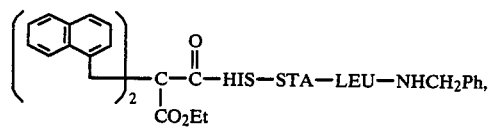

—NHCH₂CH=CH₂, —NHCH₂CH(OH)CH₂SCH(CH₃)₂,
—NHCH₂CH(OH)CH₂SOCH(CH₃)₂,
—NHCH₂CH(OH)CH₂SO₂CH(CH₃)₂, or
—NHCH₂CH(CH₃)CH₂CH₃.

3. A peptide according to claim 1 wherein the peptide is a member selected from the group consisting of DNMA—HIS—STA—LEU—NHCH₂Ph,

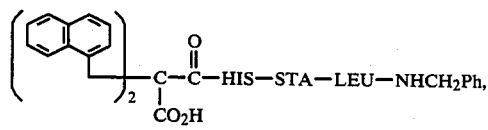

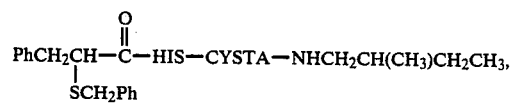

PhCH₂CH(SCH₂Ph)—C(=O)—HIS—CYSTA—NHCH₂CH(CH₃)CH₂CH₃,

-continued

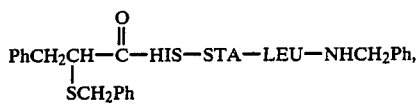

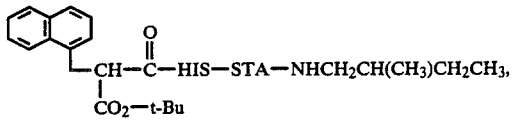

DNMA—HIS—STA—NHCH₂CH=CH₂,

DNMA—HIS—STA—NHCH₂CH(OH)CH₂SCH(CH₃)₂,

DNMA—HIS—STA—NHCH₂CH(OH)CH₂SO₂CH(CH₃)₂,

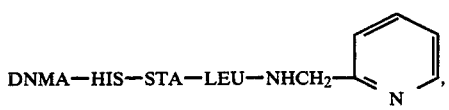

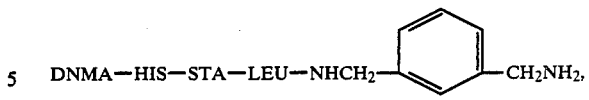

DNMA—HIS—CYSTA—LEU—NHCH₂Ph, or
DNMA—HIS—STA—(N—MeLEU)—NHCH₂Ph.

4. A pharmaceutical composition comprising a renin-inhibitory effective amount of a compound as claimed in claim 1 together with a pharmaceutically acceptable carrier.

5. A method of treating renin-associated hypertension which comprises administering to a mammal a pharmaceutical composition as claimed in claim 4.

6. A pharmaceutical composition comprising an hyperaldosteronism-inhibitory effective amount of a compound as claimed in claim 1 together with a pharmaceutically acceptable carrier.

7. A method of treating hyperaldosteronism which comprises administering to a mammal a pharmaceutical composition as claimed in claim 6.

8. A method of determining the presence of renin-associated hypertension in a patient which comprises administering to said patient, at a hypotensive dosage level and as a single dose, a peptide of claim 1, followed by monitoring of said patient's blood pressure.

* * * * *